US010088391B2

(12) United States Patent
Centeno et al.

(10) Patent No.: US 10,088,391 B2
(45) Date of Patent: Oct. 2, 2018

(54) BLOOD AND MARROW DRAW PROCESSING DEVICES AND METHODS

(71) Applicant: Regenerative Sciences, LLC, Broomfield, CO (US)

(72) Inventors: Christopher J. Centeno, Broomfield, CO (US); Brian Leach, Broomfield, CO (US); Ryan Dregalla, Broomfield, CO (US); Patrick Reischling, Broomfield, CO (US)

(73) Assignee: Regenexx, LLC, Broomfield, CO (US)

( * ) Notice: Subject to any disclaimer, the term of this patent is extended or adjusted under 35 U.S.C. 154(b) by 273 days.

(21) Appl. No.: 14/767,679

(22) PCT Filed: Feb. 18, 2014

(86) PCT No.: PCT/US2014/016814
§ 371 (c)(1),
(2) Date: Aug. 13, 2015

(87) PCT Pub. No.: WO2014/130426
PCT Pub. Date: Aug. 28, 2014

(65) Prior Publication Data
US 2016/0003712 A1    Jan. 7, 2016

Related U.S. Application Data

(60) Provisional application No. 61/767,385, filed on Feb. 21, 2013.

(51) Int. Cl.
*G01N 1/14* (2006.01)
*A61B 5/15* (2006.01)
(Continued)

(52) U.S. Cl.
CPC ........... *G01N 1/14* (2013.01); *A61B 5/15003* (2013.01); *A61B 5/153* (2013.01);
(Continued)

(58) Field of Classification Search
CPC ..... G01N 1/14; B01D 21/262; A61M 1/3693; B01L 3/5021; B01L 2300/0858;
(Continued)

(56) References Cited

U.S. PATENT DOCUMENTS 3,965,889 A * 6/1976 Sachs ................. A61B 5/15003
210/789
4,479,578 A * 10/1984 Brignola ............... A61J 1/2093
206/221
(Continued)

FOREIGN PATENT DOCUMENTS

WO    WO 2007050986 A1 * 5/2007 ............ B01L 3/5021

OTHER PUBLICATIONS

International Search Report and Written Opinion dated May 7, 2014 for International Application No. PCT/US14/016814.

*Primary Examiner* — Walter D. Griffin
*Assistant Examiner* — Shuyi S. Liu
(74) *Attorney, Agent, or Firm* — Swanson & Bratschun, L.L.C.

(57) ABSTRACT

Apparatus, systems and methods for processing a blood sample. One embodiment comprises an isolation container having at least one sidewall defining an interior volume. The interior volume includes a medial reservoir in fluid communication with proximal and distal reservoirs. The diameter of the medial reservoir is less than the diameter of the proximal and distal reservoirs. Therefore, the isolation container has an interior volume which is roughly hour-glass shaped with the medial reservoir being a substantially narrowed portion or channel between two wider portions. The isolation container is configured such that the buffy coat layer of fractionated blood will be located within and may be accessed from the reduced cross sectional medial reservoir after a centrifuge or other processing step.

22 Claims, 10 Drawing Sheets

(51) Int. Cl.
  *B01L 3/00* (2006.01)
  *A61M 1/36* (2006.01)
  *B01D 21/26* (2006.01)
  *A61B 5/153* (2006.01)

(52) U.S. Cl.
  CPC .. *A61B 5/150213* (2013.01); *A61B 5/150236* (2013.01); *A61B 5/150244* (2013.01); *A61B 5/150251* (2013.01); *A61B 5/150755* (2013.01); *A61B 5/150908* (2013.01); *A61M 1/3693* (2013.01); *B01D 21/262* (2013.01); *B01L 3/5021* (2013.01); *B01L 2300/0858* (2013.01); *B01L 2300/0864* (2013.01)

(58) Field of Classification Search
  CPC ....... B01L 2300/0864; A61B 5/150213; A61B 5/150236; A61B 5/150244; A61B 5/15003; A61B 5/150755; A61B 5/150908; A61B 5/153; A61B 5/150251
  USPC ........................................ 494/10, 37, 16, 20
  See application file for complete search history.

(56) References Cited

U.S. PATENT DOCUMENTS

| | | |
|---|---|---|
| 5,086,784 A | 2/1992 | Levine |
| 5,251,474 A | 10/1993 | Wardlaw |
| 5,393,301 A * | 2/1995 | Goldberg ............ A61M 5/3202 604/110 |
| 5,393,674 A | 2/1995 | Levine |
| 5,955,032 A | 9/1999 | Kelly |
| 6,280,400 B1 | 8/2001 | Niermann |
| 6,406,671 B1 | 6/2002 | DiCasare |
| 7,077,827 B2 | 7/2006 | Greenfield |
| 7,220,593 B2 | 5/2007 | Haubert |
| 7,329,534 B2 | 2/2008 | Haubert |
| 7,354,515 B2 | 4/2008 | Coull |
| 7,358,095 B2 | 4/2008 | Haubert |
| 7,629,176 B2 | 12/2009 | Haubert |
| 7,915,029 B2 | 3/2011 | Haubert |
| 7,919,049 B2 | 4/2011 | Haubert |
| 8,012,742 B2 | 9/2011 | Haubert |
| 8,048,678 B2 * | 11/2011 | Duffy, Jr. .............. B01L 3/5021 210/513 |
| 8,114,680 B2 | 2/2012 | Haubert |
| 8,313,954 B2 | 11/2012 | Leach |
| 2015/0004080 A1 * | 1/2015 | Hassouneh ............ B01L 3/508 422/548 |
| 2016/0298076 A1 * | 10/2016 | Centeno ................ A61M 1/029 |

* cited by examiner

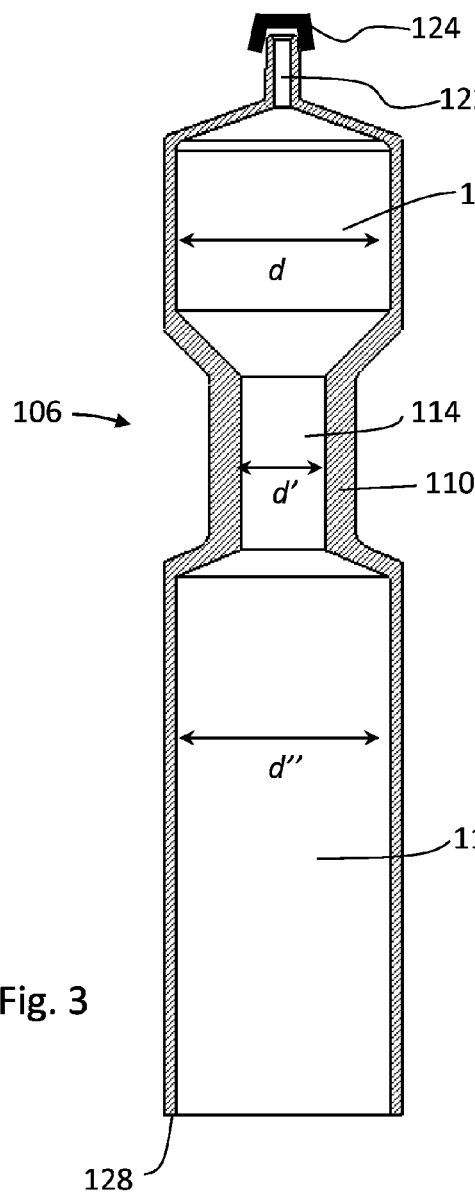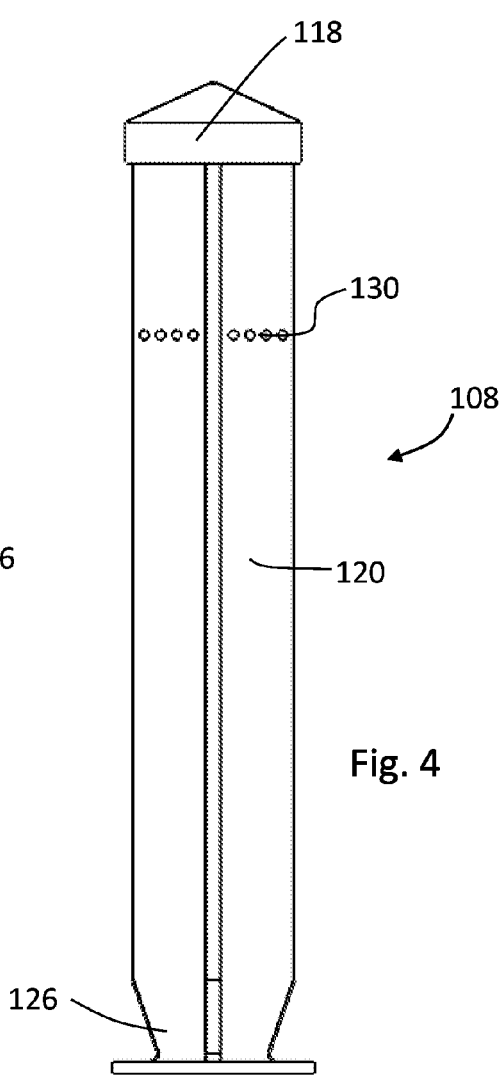
Fig. 3
Fig. 4

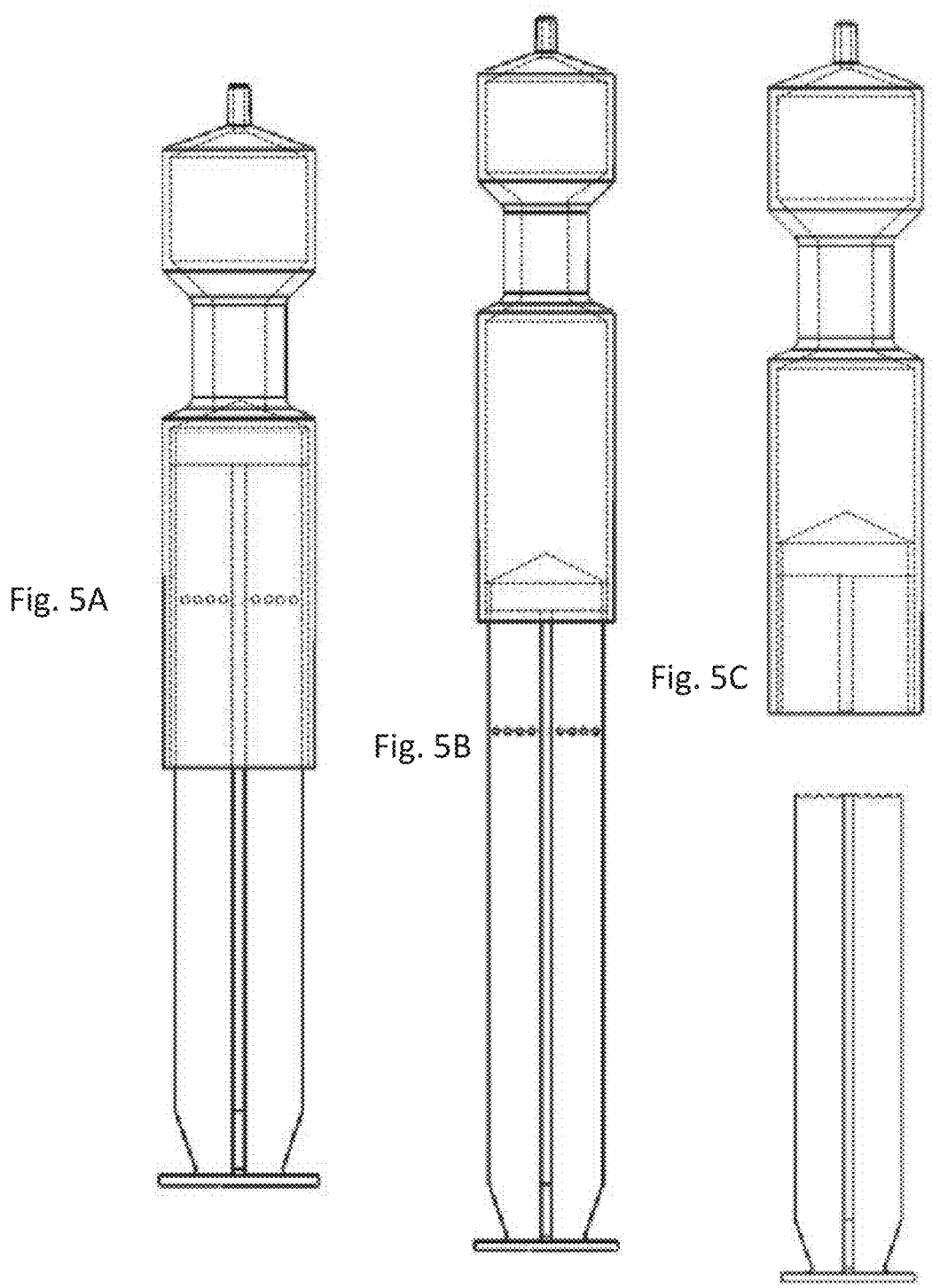

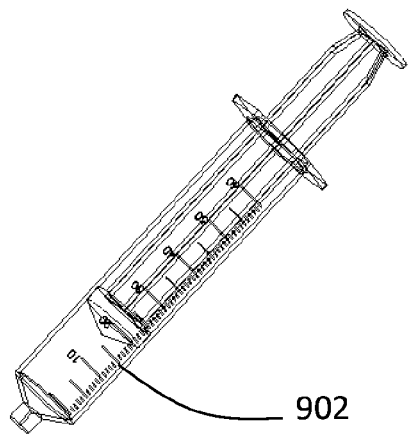
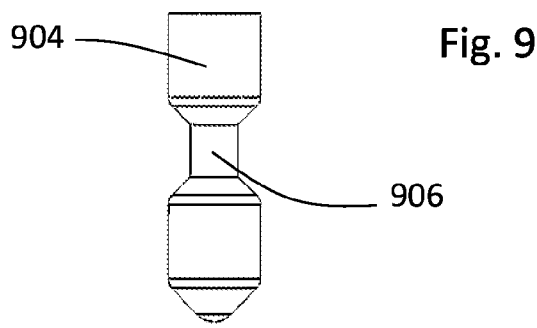
Fig. 9
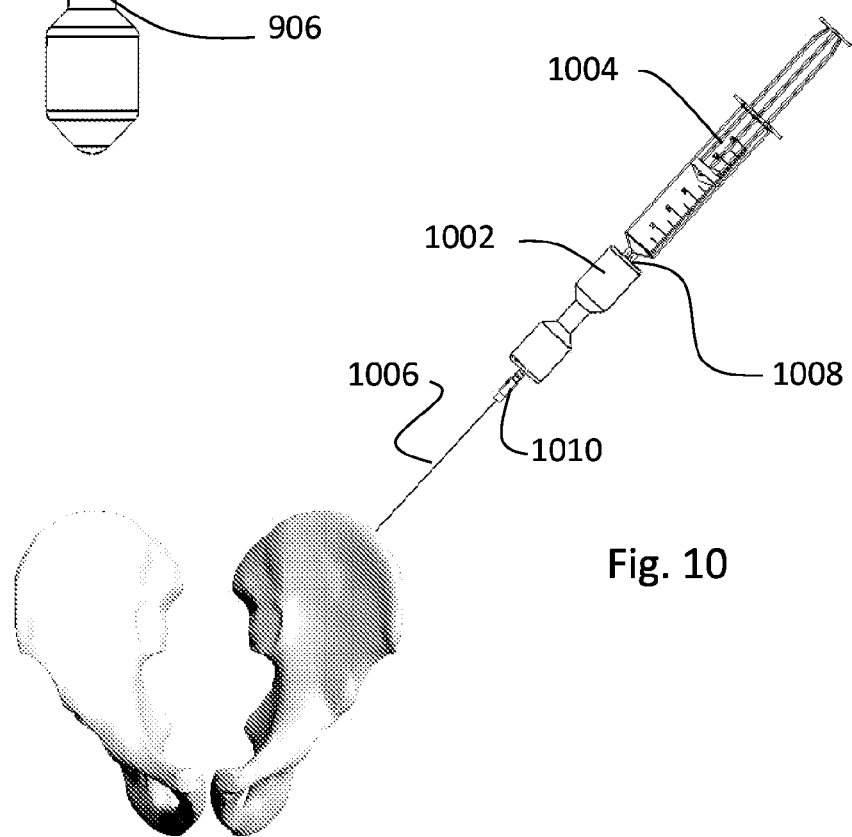
Fig. 10

BLOOD AND MARROW DRAW PROCESSING DEVICES AND METHODS

RELATED APPLICATIONS

This application is a 35 U.S.C. § 371 national phase application of PCT/US14/16814 (WO 2014/130426), filed on Feb. 18, 2014, entitled "Blood and Marrow Draw Processing Devices and Methods", which application claims the benefit of U.S. Provisional Application Serial No. 61/767,385, filed Feb. 21, 2013, which is incorporated herein by reference in its entirety.

FIELD OF THE INVENTION

The invention generally relates to devices and methods for drawing blood or marrow from a patient, separating the blood into density graded fractional layers and isolating selected layers. The disclosed embodiments more particularly may be used to draw, separate and isolate the buffy coat layers from a peripheral blood, marrow blood or whole marrow sample.

BACKGROUND OF THE INVENTION

There are many procedures and processes that require the separation of blood into blood components or density graded layers. As used herein, "blood" may include peripheral blood, marrow blood or whole marrow. Known methods include density gradient additives which expand portions of the blood, discrete sample centrifugation, and continuous centrifugal separation. Separation of blood products may be required for diagnostic tests, blood donation, transfusions, or autogenic therapeutic reasons. The constituent components of a fractioned blood sample, listed from upper-most (least dense) to lower-most (highest density) fractions when a density separation is viewed from the side, are as follows: platelet-poor plasma, platelet-rich plasma, the "buffy coat" and red blood cells (RBCs). The buffy coat is the separated blood portion that contains the white blood cells, platelets, mesenchymal stem cells, hematopoietic stem cells, macrophages, adipocytes, osteoblasts, endothelial progenitor cells, very small embryonic like stem cells, blastomere like stem cells, and other nucleated cells.

Several techniques have been developed to isolate of the above noted fractions. Some of these techniques are substantially automated and performed by machine. Other techniques use substantially manual and feature centrifugation followed by some degree of manual post-processing to isolate the fractions. Alternative techniques involve manual isolation of centrifuged blood sample fractions using standard laboratory equipment and aseptic techniques. For example, as shown in FIG. 1 (Prior Art) a 50 cc or other appropriately sized conical tube is often used with centrifugation to fractionate a blood sample. There are benefits and shortcomings to each of the conventional blood fractionation methods. Some of the metrics used as indicators of the effectiveness of an isolation performance are as follows; time required to process blood, percentage of available fraction isolated, technician skill required to successfully produce quality isolations, and cross-contamination risk between isolated fractions.

As noted above, one blood fraction of interest is the buffy coat. The buffy coat is the separated portion of an un-coagulated blood sample that contains most of the nucleated cells, including but not limited to white blood cells, platelets, mesenchymal stem cells, hematopoietic stem cells, macrophages, adipocytes, osteoblasts, endothelial progenitor cells, very small embryonic like stem cells, blastomere like stem cells, and other nucleated cells after density gradient centrifugation. Typically, the buffy coat makes up less than 1% of the total volume of a blood sample. Although the buffy coat is predominately composed of white blood cells and platelets, the buffy coat also contains the various types of stem cells listed above. Stem cells, including mesenchymal stem cells (MSCs) are pluripotent blast or embryonic-like cells located in blood, bone marrow, dermis and periosteum. In general these cells are capable of renewing themselves over extended periods of time as well as, under various environmental conditions, differentiating into cartilage, bone and other connective tissue. In this manner MSCs and other types of stem cells have been reported to have regenerative capabilities in a number of animal models.

Further, these finding are being extended in clinical trials to humans. Typical MSC therapies must be initiated with a source of autologous or non-autologous MSCs, and the proposed therapy can feature in vitro or in vivo MSC expansion. In view of the relatively tiny volume of the buffy coat and the relatively tiny quantity of MSCs in the buffy coat, it is useful to efficiently extract as much of the buffy coat from a sample as is possible in an aseptic and waste free manner.

The present invention is directed toward overcoming one or more of the problems discussed above.

SUMMARY OF THE EMBODIMENTS

The embodiments disclosed herein include apparatuses, systems and methods for processing a blood sample. One apparatus embodiment comprises an isolation container having at least one sidewall defining an interior volume. The interior volume of the isolation container includes a proximal reservoir having a select diameter. The interior volume also includes a medial reservoir in fluid communication with the proximal reservoir. The diameter of the medial reservoir is less than the diameter of the proximal reservoir. The interior volume also includes a distal reservoir in fluid communication with the medial reservoir with the distal reservoir having a diameter which is greater than the diameter of the medial reservoir. Therefore the isolation container has an interior volume which is roughly hour-glass shaped with the medial reservoir being a substantially narrowed portion or channel between two wider portions.

The isolation container also includes a plunger in sealing and slidable engagement with the side walls of the distal reservoir and a coupling in fluid communication with the proximal end of the proximal reservoir. The plunger may in certain instances be a one-piece element fabricated from plastic or another material, more typically however; the plunger may include a sealing element fabricated from an elastomeric material in slidable engagement with the side walls and a handle attached to the sealing element. In use, a portion of the handle will initially extend beyond the distal end of the distal reservoir. Thus, the plunger and distal reservoir may be manipulated in the manner of a conventional syringe to draw a fluid such as blood into the interior volume of the isolation container.

In certain embodiments, at least a portion of the handle may be selectively removed from the remaining portion or portions of the plunger. For example, the handle may include a series of perforations defining one or more break-lines at which a portion of the handle may be conveniently removed. A break-line or break-plane formed as described above may also be used to define a specific selected volume within the isolation container. For example, the break-plane may be made coplanar with a plane defined by the distal end of the sidewall of the distal reservoir, thus defining a selected volume within the isolation container.

Alternative embodiments of the apparatus for processing a blood sample include an isolation container having a port which opens into the medial reservoir. Alternatively, the isolation container may include an internal or external lumen which opens into the medial reservoir. In certain embodiments the position of the port or lumen opening may be adjusted axially toward or away from the proximal and distal reservoirs.

In use, blood, bone marrow or combination of blood and marrow may be drawn into the isolation container by withdrawing the plunger. The blood or marrow may be drawn from any mammalian blood or marrow source. The isolation container may then be sealed or capped and placed directly into a centrifuge to fractionate the blood or marrow into density graded layers. The isolation container is sized such that the buffy coat layer of fractionated blood will be located within the reduced cross sectional medial reservoir after the centrifuge step. In this manner the axial length of the buffy coat is increased, facilitating efficient withdrawal. It is known that the percentage of hematocrits (red blood cells) in a blood sample will vary widely from patient to patient. Thus, a blood processing system may include a selection of two, three or several isolation containers having various internal volumes and internal volume configurations which may be matched with sample size and patient hematocrit levels to assure proper placement of the buffy coat after centrifugation. Alternatively, or in conjunction with the selection of an appropriately sized isolation container, the sample volume may be adjusted to place the layer of interest, for example the buffy coat, within the reduced diameter medial reservoir where the buffy coat is most accessible after centrifugation is complete.

After the centrifuge step, a technician may withdraw the buffy coat from the balance of the sample through the port or lumen if a port or lumen is provided, or using a pipette, needle, suction or other technique which can be used to access the medial reservoir.

The disclosed embodiments are particularly useful for drawing marrow or blood from a patient, processing the sample on site to isolate the buffy coat and re-injecting the buffy coat and mesenchymal stem cells (MSCs) contained therein into the patient for therapeutic purposes. Thus, the disclosed embodiments are optimized to minimize sample transfers, sample waste, contamination risk and processing delays.

In certain apparatus embodiments it will be useful for a technician to visually observe the location of the buffy coat within the medial reservoir. Accordingly, certain apparatus embodiments are provided with at least a medial reservoir sidewall manufactured from a transparent material.

Alternative apparatus embodiments include but are not limited to stand-alone isolation containers substantially as described above but without a proximal coupling. In this embodiment blood or marrow may be placed into the isolation container for further processing, directly from a conventional syringe. Alternatively, an isolation container having a proximal coupling and a distal coupling may be placed in-line between a trocar, needle, catheter or other fluid pathway and a conventional syringe such that the isolation container may be filled by causing a partial vacuum in the entire system by operating the syringe.

Several system embodiments are also disclosed. System embodiments include an isolation container or series of volume graded isolation containers plus a trocar, needle, catheter, associated tubing and other elements required to place the isolation container into fluid communication with a source of blood or marrow. The system may also include a centrifuge configured to directly receive the isolation container eliminating the need to transfer the blood or marrow sample to a separate centrifuge container.

Alternative disclosed embodiments include methods of using the disclosed systems and apparatus to process a blood sample. In particular, method embodiments include drawing or otherwise placing blood or marrow into an isolation container, centrifuge and the contents of the isolation container and withdrawing a selected density-graded layer (typically the buffy coat) from the isolation container. The method may further include injecting the buffy coat, or a portion of the buffy coat, for example MSCs, into a patient for therapeutic purposes. The disclosed apparatus thus provides a method for withdrawing, processing and effectively withdrawing a portion of a fractionated blood or marrow sample using one isolation container for several processing steps, thus minimizing waste and contamination risk. In addition, the steps of the disclosed methods, including re-injecting material into a patient for therapeutic purposes may be performed in one visit to a single treatment facility.

BRIEF DESCRIPTION OF THE DRAWINGS

FIG. 3 is a plan cross sectional view of a isolation container as disclosed.

FIG. 4 is a plan sectional view of a plunger as disclosed.

FIGS. 5A, 5B, and 5C are a series of plan view illustrations of a blood processing apparatus as disclosed in various operational states.

FIG. 9 is schematic illustration of an alternative blood processing system as disclosed.

FIG. 10 is schematic illustration of an alternative blood processing system as disclosed.

DETAILED DESCRIPTION OF THE EMBODIMENTS

Embodiments disclosed herein include an apparatus for processing a blood or marrow sample, various blood sample processing systems, and methods of processing a blood sample. The disclosed apparatus, systems and methods may be used to draw blood from a mammalian patient, separate the blood into density graded layers and isolate layers of interest. The disclosed apparatus, systems and methods are optimized to minimize the necessity for transferring a blood sample from or between various containers during processing. A "blood sample" is defined herein as a quantity of blood drawn from a mammal including but not limited to a human. The blood sample may be a peripheral blood sample drawn from a vein or artery. Alternatively the blood sample may be a marrow blood sample or whole marrow drawn from a source of marrow within bone tissue.

Figure 2:
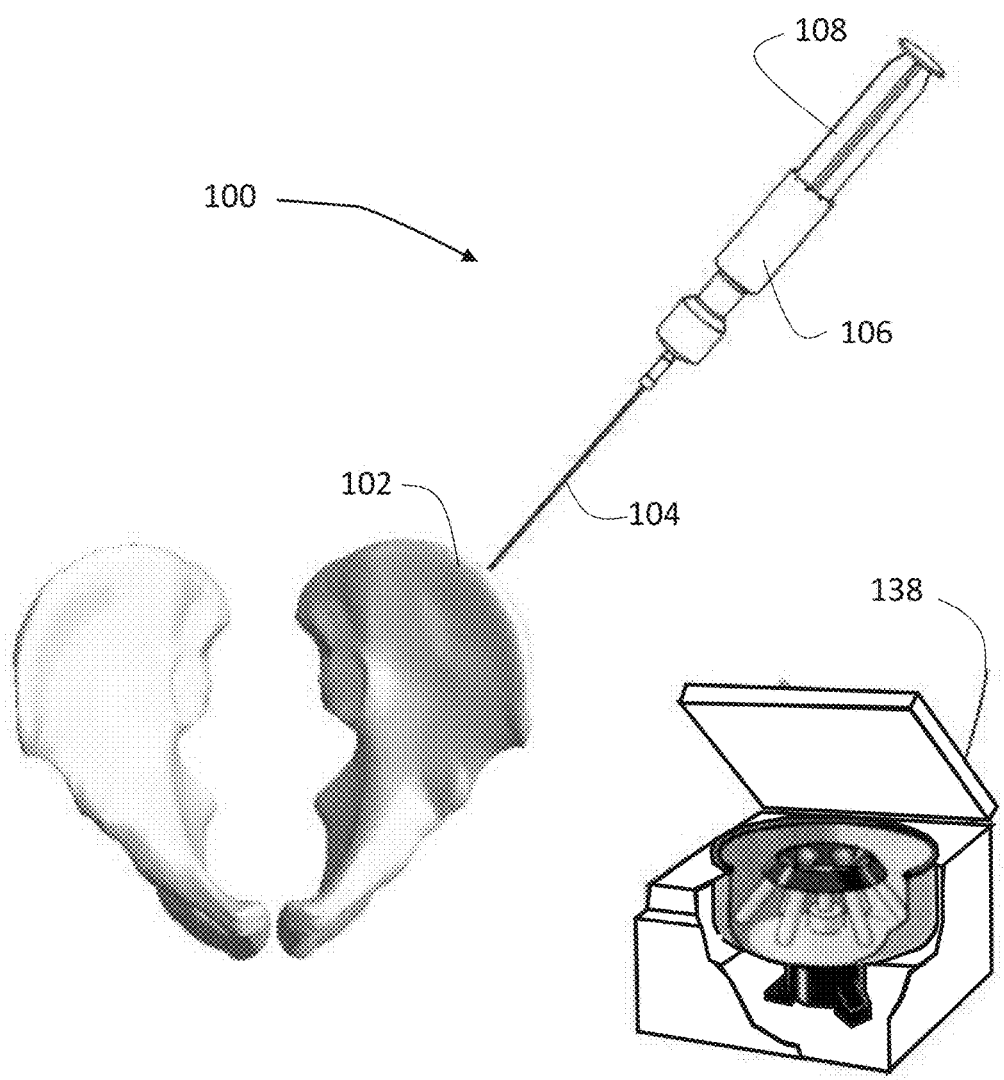
FIG. 2 is a schematic illustration of a system for processing blood.

FIG. 2 schematically illustrates an apparatus for processing blood 100 in a system configured for use. As shown in FIG. 2, the apparatus 100 may be connected to a source of marrow, blood or both, for example, the iliac crest 102 of a patient's pelvis. The apparatus may be connected to the source of blood using a trocar 104, needle, catheter or other method. Similarly, the apparatus 100 may be connected to a source of peripheral blood using known techniques.

As more particularly shown in FIGS. 3-4, the apparatus 100 may include an isolation container 106 and a plunger 108. The isolation container 106 includes at least one sidewall 110 defining an interior volume. The interior volume of the isolation container 106 includes at least three separate regions in fluid communication with each other. As shown in FIG. 3, the interior volume includes a proximal reservoir 112 having a select diameter d. The interior volume also includes a medial reservoir 114 in fluid communication with the proximal reservoir 112. The medial reservoir 114 has a diameter d' which is less than the select diameter d of the proximal reservoir 112. The interior volume also includes a distal reservoir 116 in fluid communication with the medial reservoir 114 opposite the proximal reservoir 112. The distal reservoir 116 has a diameter d" which is greater than the diameter d' of the medial reservoir 114. Although the diameters d and d" are illustrated as being roughly equivalent in FIG. 3, this configuration is not required. As described in detail below the respective diameters of the various reservoirs which comprise the isolation container can be selected to achieve desired blood processing results. In all cases however, the diameter d' of the medial reservoir 114 will be substantially less than the diameters of the remaining reservoirs. Furthermore, the term diameter as used herein does not require that the various reservoirs have a circular cross-section. Alternative embodiments may have elliptical or irregular cross-section defining at least one diameter.

The apparatus 100 also includes a plunger 108. One embodiment of plunger 108 includes a sealing element 118 and a handle 120 which may be made of distinct materials joined together. For example, the sealing element 118 may be made of rubber, silicone or another compliant material and the handle may be made of a plastic of selected rigidity. Plunger embodiments consisting of only one material or more than two materials are within the scope of this disclosure.

In use, the plunger 108 is received in sealing and slidable engagement with the side wall 110 of the distal reservoir 116. Thus, at least the periphery of the sealing element 118 and potentially more of the plunger 108 forms a substantially fluid-tight seal with the inner wall of distal reservoir 116. A seal is made while maintaining the ability of the plunger 108 to slide lengthwise toward or away from the medial and proximal reservoirs. Thus, the plunger 108 and distal reservoir 116 in the FIG. 3-4 embodiment function like a syringe such that moving the plunger 108 away from the medial and proximal reservoirs causes a partial vacuum which can be employed to draw a blood sample into the isolation container 106.

The FIG. 3-4 embodiment also includes a coupling 122 in fluid communication with the proximal reservoir 112. The coupling may be, but is not limited to, a standard Luer-type coupling which facilitates attachment to a trocar, catheter, needle or other device. At certain times during the processing of a blood sample, the coupling 122 may be sealed with a cap 124.

FIG. 4 provides a detailed view of one embodiment of plunger 108. As noted above the plunger may include a compliant sealing element 118 and handle 120. The handle may include a grip structure 126 which, in use, extends beyond a distal sidewall surface 128 of the distal reservoir 116. It may be advantageous for effective blood sample processing to remove a portion of the handle 120 (or a portion of plunger 108 in single plunger material embodiments) prior to performing certain processing steps. For example, the isolation container 106 and plunger 108 may fit more readily into a centrifuge if a portion of the handle 120 is removed. Alternatively, a system may include a centrifuge configured to accept the isolation container 106 and plunger 108 without handle removal or modification.

Thus, in some embodiments, the handle 120 or plunger 108 may be provided with a plurality of perforations 130, a score line, a thinned region, a glue line, a region of relatively weak material, socket and coupling, male and female screw threading or other structure which defines a break-line at which a portion of the handle may be selectively removed from a remaining portion of the handle. In the FIG. 4 embodiment, the perforations 130 continue in the handle structure extending out from the printed page, thus the perforations 130 define multiple break lines which together define a break-plane. Alternatively, the plunger may include a handle which can be unscrewed from the sealing element or otherwise disengaged from the sealing element or a lower handle portion.

As illustrated in FIGS. 5A, 5B, and 5C, the break plane (or another surface defined when a portion of the handle is removed, for example by un-screwing the handle) may be used to set and control a specific sample size volume within the isolation container 106. For example, as shown in FIG. 5A, the sealing member 118 of the plunger 108 may be placed firmly against the proximal edge of the distal reservoir 116 prior to drawing blood into the isolation container 106. Then, as shown in FIG. 5B, the plunger 108 may be withdrawn until the perforations or other elements defining a break-line are beyond the distal edge 128 of the distal reservoir 116. As then shown in FIG. 5C, The outer portion of the handle may be removed from the balance of the plunger. At this point, the break-plane defined by the perforations 130 may be made co-planar with the distal edge of the distal reservoir to precisely control the volume within the isolation container 106, between the proximal end of the coupling 122 and the proximal surface of the plunger 108.

Figure 6A:
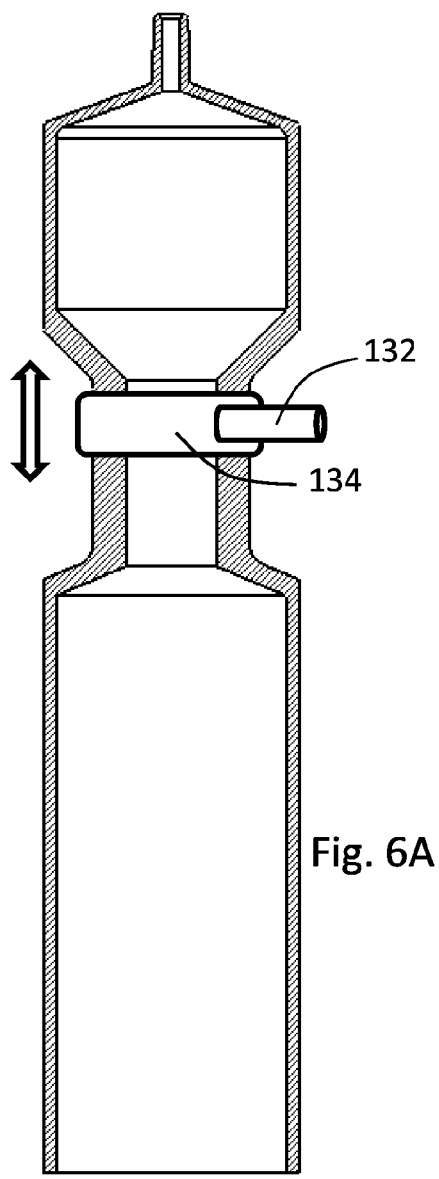
FIGS. 6A and 6B are plan cross sectional views of an alternative isolation container embodiment featuring a port or magnifying element associated with a sliding collar.

FIG. 6A illustrates an alternative embodiment of isolation container 106 further comprising a port 132 passing through a portion of the isolation container wall 110 defining the medial reservoir 114. Thus, said port 132 defines an opening directly into the medial reservoir 114 from outside the isolation container 106 without passing through the proximal reservoir 112 or the distal reservoir 116. As detailed below, the medial reservoir can serve to isolate the buffy coat or other blood fraction of interest. In embodiments including a port 132, the port facilitates the accurate withdrawal or removal of the buffy coat from other layers. In certain embodiments, the port 132 includes a collar 134, slot, lumen or other mechanism which allows the location of the port 132 to be translated axially toward the proximal reservoir or axially toward the distal reservoir to facilitate removal of the buffy coat from other layers.

Figure 6B:
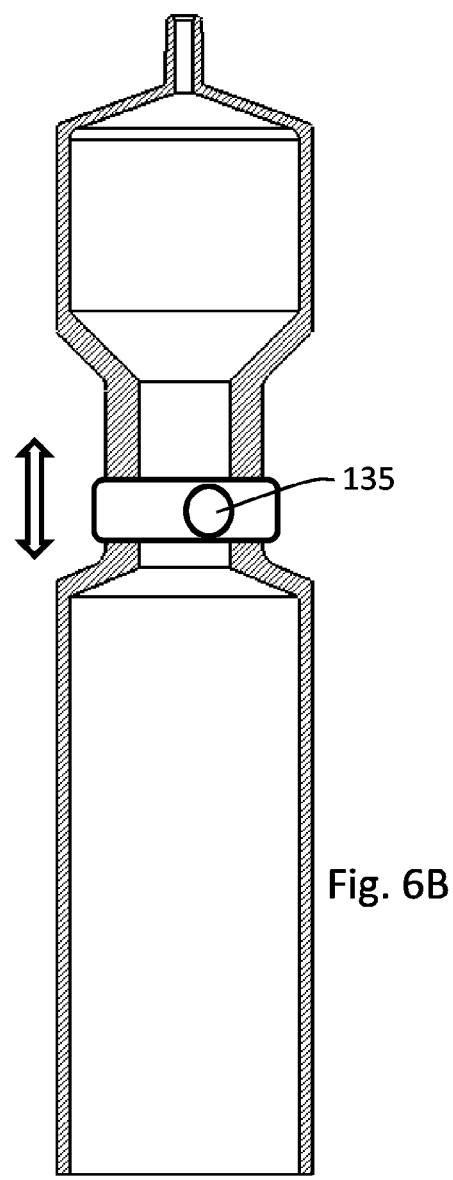

FIG. 6B illustrates an alternative embodiment where a magnifying lens 135 is associated with the isolation container wall 110 at the medial reservoir 114. In certain embodiments, the magnifying lens 135 may be slid longitudinally along the medial reservoir 114 to aid a technician with the task of identifying and subsequently effectively removing the relatively small buffy coat layer from the sample. A magnifying lens 135 may be a simple cylinder-type magnifier fabricated from glass or transparent plastic in conjunction with a sliding collar 134 as shown in FIG. 6B. Alternatively the magnifying lens could be a more complex optical element having precision lens components. In certain embodiments, the magnifying lens 135 and a port 132 may both be provided as a single structure or multiple structures operatively connected to a single collar 134.

Figure 7:
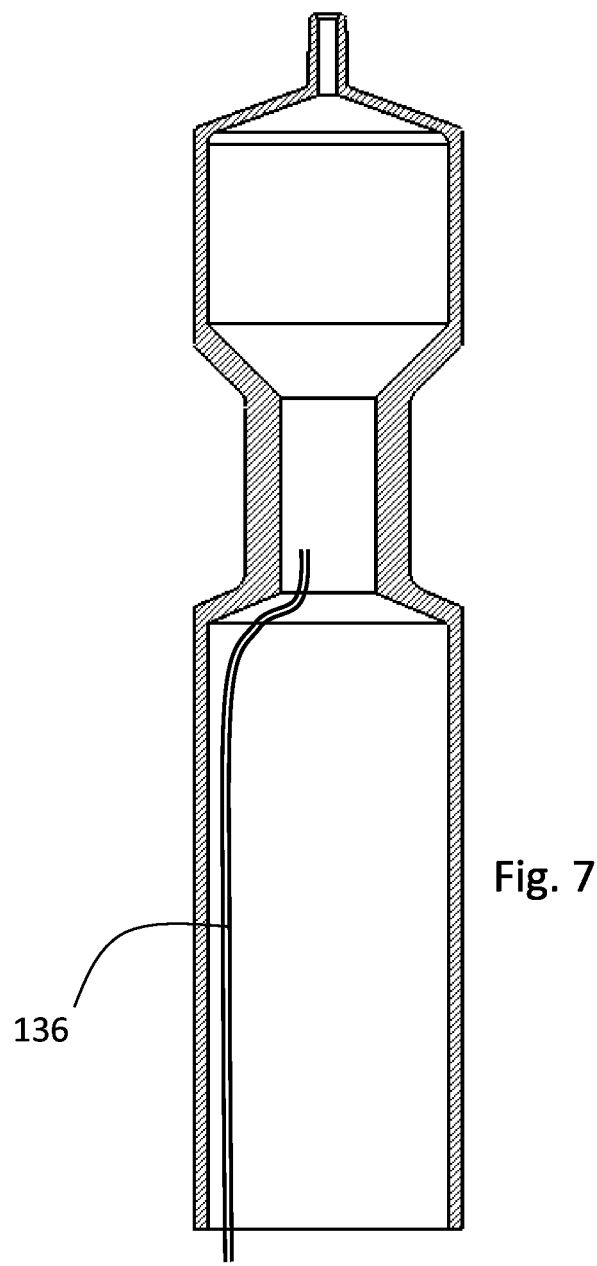
FIG. 7 is a plan cross sectional view of an alternative isolation container embodiment featuring a lumen.

FIG. 7 illustrates an embodiment of isolation container 106 including an inner lumen 136 having an opening at one end which is in fluid communication with the medial reservoir 114. In selected embodiments featuring an inner lumen 136, the position of the inner lumen opening may be translated within the medial reservoir axially toward or away from the proximal and distal reservoirs. The inner lumen 136 may be used to efficiently remove the buffy coat or other selected blood fraction from other layers.

Certain embodiments of isolation container 106 will be subjected to one or more manual or operator guided processing steps. Accordingly, it may be advantageous in certain embodiments to fabricate the sidewall 110, in at least the region of the medial reservoir 114, from an optically transparent material.

The isolation container 106 may (in conjunction with a plunger 108) and other apparatus such as a trocar, be used to directly drawn marrow or peripheral blood from a patient. Alternatively, as noted below, other embodiments of isolation container may receive blood drawn by other means. In either case, the isolation container 106 may be part of a blood sample processing system. As shown in FIG. 2, a system may include the apparatus 100 and in particular an isolation container 106, a trocar 104 or other fluid pathway to a source of blood, and a centrifuge 138. The centrifuge 138 may directly receive the isolation container 106 to minimize blood handling, contamination risk and transfer waste. Prior to placement in the centrifuge 138 the openings to the isolation container 106 may be sealed with a cap 124 and plunger sealing elements 118 as described above or through other means. The blood contained within the isolation container 106 may then be centrifuged such that the sample develops density-graded layers within the isolation container.

Figure 8:
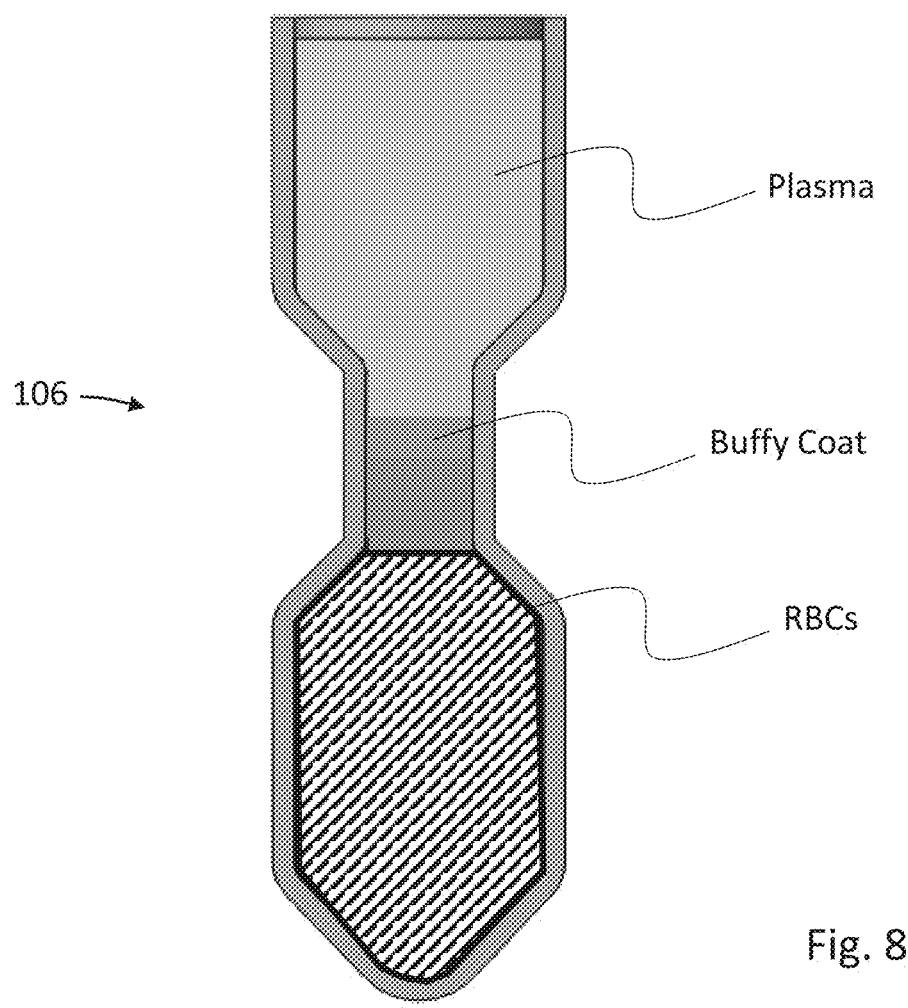
FIG. 8 is a schematic illustration of blood fractioned in isolation container as disclosed.

As shown in FIG. 8, the isolation container 106 will typically be sized such that the buffy coat will be located within the reduced cross sectional medial reservoir 114 independent of hematocrits after a centrifuge step. In this manner the axial size of the buffy coat is increased, facilitating withdrawal. It is known that the percentage of hematocrits (red blood cells) in a blood sample will vary widely from patient to patient. Thus, a blood processing system may include a selection of two, three or several isolation containers 106 having various internal volumes and configurations which may be matched with sample size and patient hematocrit levels. Alternatively, or in conjunction with the selection of an appropriately sized isolation container 106, the sample volume may be adjusted to place the layer of interest, for example the buffy coat, within the reduced diameter medial reservoir 114 where the buffy coat is most accessible after centrifugation is complete. The medial reservoir 114 of the isolation container will typically occupy 10-20% of the total volume of the container. The remaining volume will be split between the proximal reservoir and distal reservoir of the isolation container with the proximal reservoir containing 1-8% more volume than the distal reservoir, because RBC percentage of blood ranges from 42-48%.

The disclosed embodiments are particularly useful for drawing marrow or blood from a patient, processing the sample on site and re-injecting the buffy coat and MSCs into the patient for therapeutic purposes. Thus, the disclosed embodiments are optimized to minimize sample transfers, waste, contamination risk and processing delays.

After the isolation container 106 has been centrifuged for a predetermined amount of time, it may be removed from the centrifuge. A technician may remove the cap 124 or seal and inserts a probe, needle, pipette or other device into the medial reservoir 114 to draw the buffy coat from the sample. In embodiments featuring a port 132 or inner lumen 136, the buffy coat or other layer of interest may be directly withdrawn through the port or inner lumen. If a magnifying element 133 is provided as shown in FIG. 6B, the technician may use the magnifier to better visualize the buffy coat and assure complete and efficient removal of same. One skilled in the art will recognize that there are a variety of methods and devices that may be used to draw the fluid buffy coat from the isolation container 106. A standard syringe may be used to draw fluid out of the isolation container, a serological pipetter may be used to draw fluid into a pipette, a powered vacuum system operated by a technician may be used to draw fluid into a reservoir, or a system employing siphon functionality may be used to draw fluid into a reservoir.

FIG. 9 illustrates an alternative embodiment where blood is drawn into a standard syringe 902 using standard methods. The syringe 902 may then be detached from the trocar and the blood contained in the syringe is emptied into an isolation container 904 which may not have a proximal coupling. The isolation container functions as described above and is centrifuged such that the buffy coat or other layer of interest is located in the reduced diameter medial reservoir 906 of the device. The technician can now use one of the many techniques described herein to remove the buffy coat from the blood sample.

FIG. 10 shows another system embodiment. An intermediate isolation container 1002 is operatively positioned between a standard syringe 1004 and a trocar 1006, needle, catheter or other conduit inserted into the patient. The syringe 1004 is operated such that blood is drawn into the intermediate isolation container 1002. Once a predetermined amount of blood has been drawn into the isolation container, the syringe 1004 is disconnected from the isolation container 1002. A cap or suitable seal is placed over the distal opening 1008 of the isolation container. In addition, the isolation container 1002 is disconnected from the trocar 1006. A cap or suitable seal is placed over the proximal connector 1010. In certain embodiments, a flexible tube may be employed such that the isolation container 1002 is able to be oriented such that the proximal connector opening is vertical, preventing spillage of the fluid when the disconnection is made. The container 1002 may then be placed into a centrifuge and spun as described above. A technician may use procedures described herein to remove the buffy coat.

The devices, apparatus, systems and methods described herein may be used to process a blood sample such that the buffy coat may be efficiently isolated and extracted. Mesenchymal stem cells (MSCs) are predominantly located within the buffy coat of a blood or whole marrow sample. MSCs are pluripotent blast or embryonic-like cells located in blood, bone marrow, dermis and periosteum. In general these cells are capable of renewing themselves over extended periods of time as well as, under various environmental conditions, differentiating into cartilage, bone and other connective tissue.

EXAMPLES

Example 1

Figure 1:
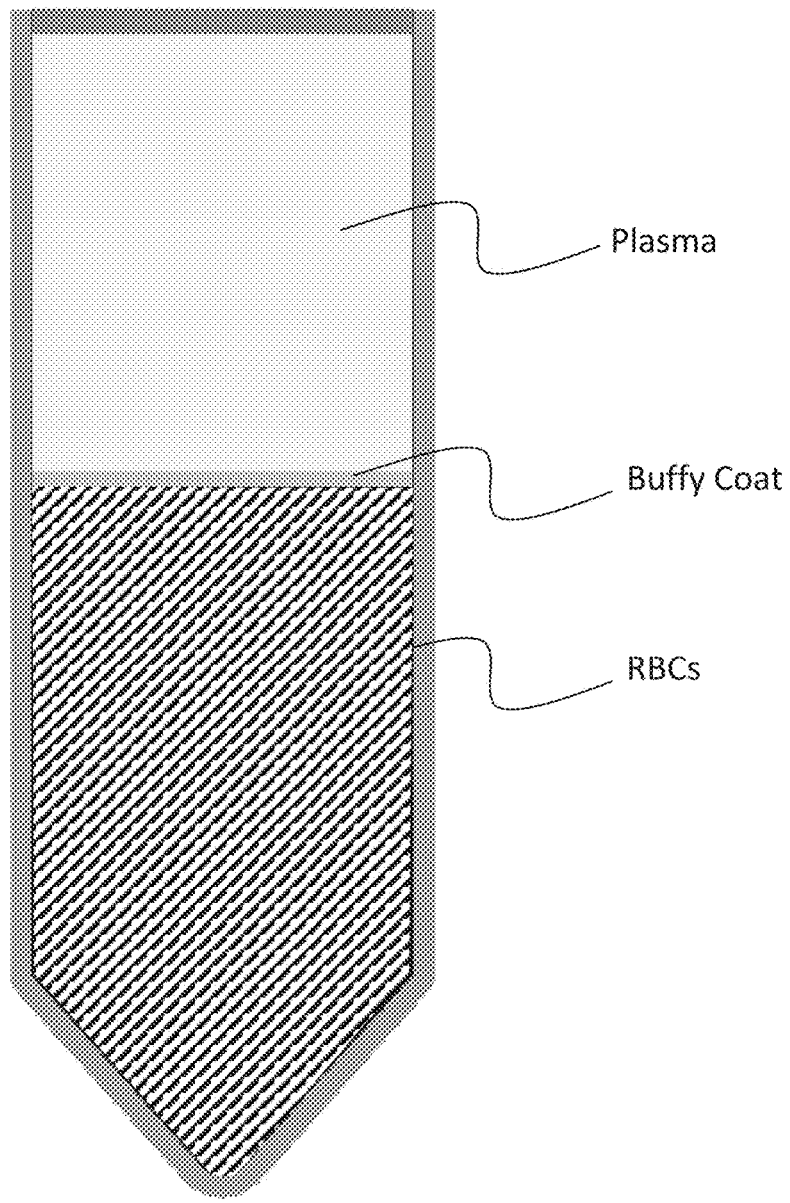
FIG. 1 is a schematic illustration of blood fractioned in a prior art processing tube.
Figure 11:
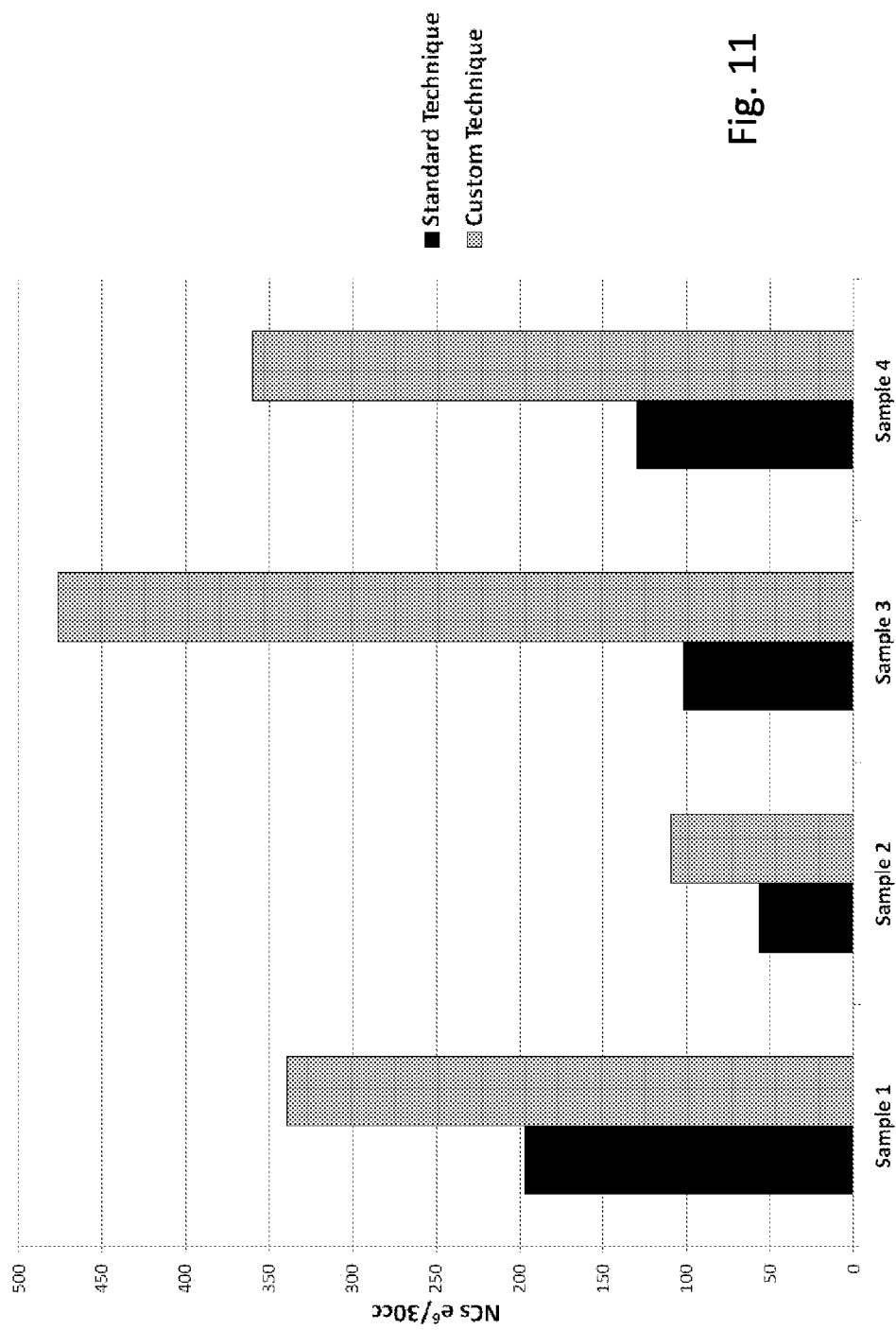
FIG. 11 is a graph comparing the results of a marrow draw and separation performed with conventional techniques compared to a marrow draw and separation performed with selected disclosed techniques.
Figure 12:
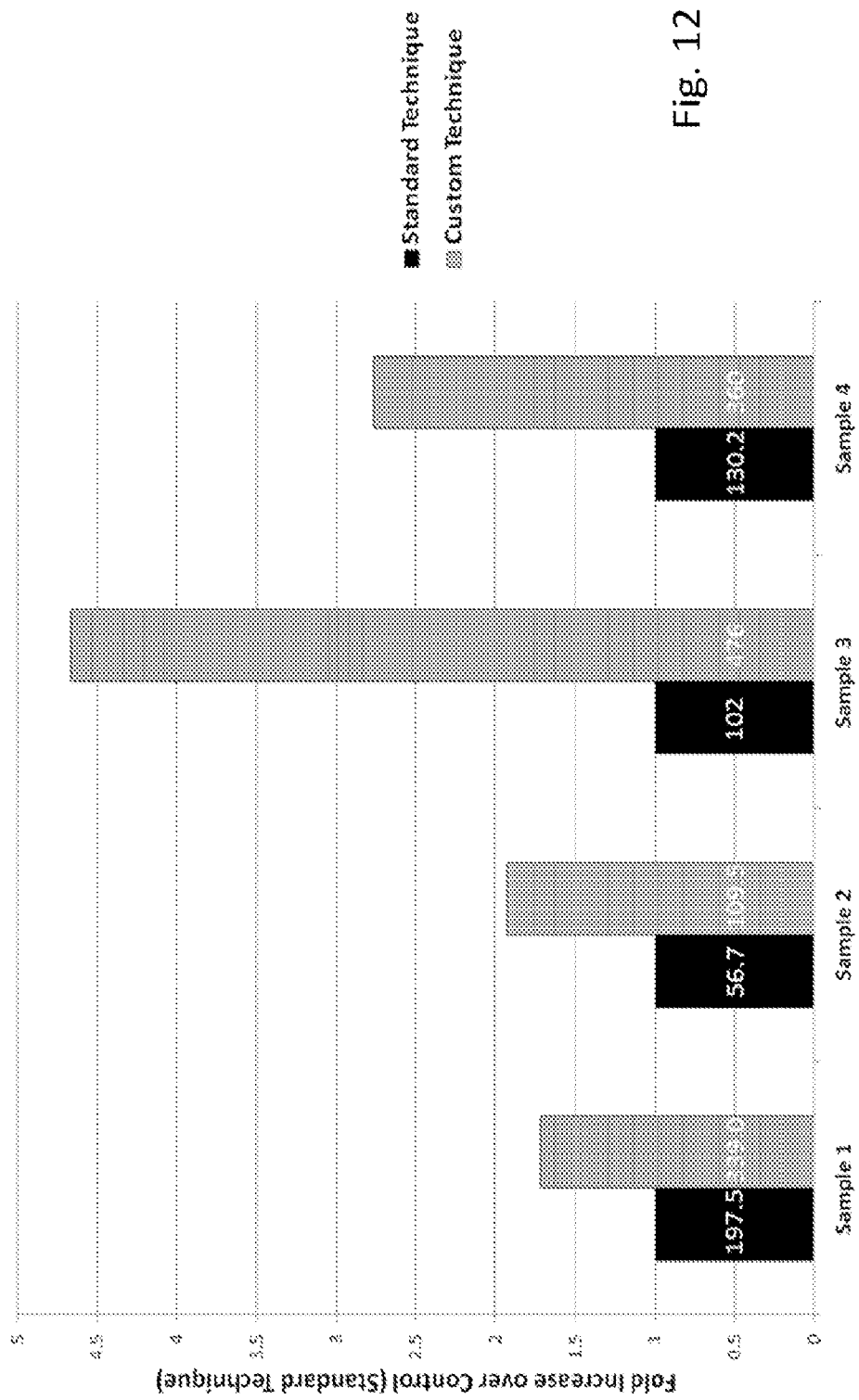
FIG. 12 is a graph showing the improvement realized with a marrow draw and separation performed with conventional techniques compared to a marrow draw and separation performed with selected disclosed techniques.

Comparison of Nucleated Cell (Buffy Coat) Recovery Using Conventional and Disclosed Techniques FIGS. 11-12 graphically illustrate the enhanced effectiveness of collecting a buffy coat when using the methods, apparatus and systems described herein as compared to standard techniques used to collect the buffy coat from a conventionally processed blood or marrow sample.
Conventional Technique:

A marrow draw sample is typically sent to a processing laboratory from the procedure room. The marrow sample of Example 1 comprises two 30 cc syringes for a total marrow volume of 60 cc to be processed. There was also extracted an additional 10 cc syringe of marrow that was used for quality assurance, but not used in the sample preparation. The marrow was placed into two (2) 50 cc conical tubes similar to those illustrated in FIG. 1. These conical tubes were placed into a standard lab centrifuge and centrifuged at a force of 200 g (calculated from rotor diameter and RPM) for 6 minutes. A BD Falcon serological pipette was used to remove the buffy coat from the two 30 mL conical tubes and subsequently the buffy coat was placed into a 15 mL conical tube. This 15 mL conical tube was placed onto the centrifuge and spun for 6 minutes at 200 g. After this second centrifuge step, there was about 1 mL of buffy coat material within the 15 mL conical tube. The operator drew out the buffy coat with a serological pipetter resulting in about 1.5 mL of material for analysis.
Disclosed Technique The disclosed technique was tested with a prototype isolation container and plunger similar to that disclosed in FIGS. 1-3. The testing of the device did not involve drawing marrow from a live patient, although the prototype was designed with that capability. As noted above, the disclosed embodiments are particularly useful for drawing marrow or blood from a patient, processing the sample on site and re-injecting the buffy coat and MSCs into the patient for therapeutic purposes. Thus, the disclosed embodiments are optimized to minimize sample transfer, waste and processing delays.

Since the device was not tested on a live patient, marrow was inserted into the device through the distal opening. The volume of marrow inserted into the device was accurately measured so that positioning of the buffy coat would fall within the reduced diameter medial reservoir of the isolation container after use of the centrifuge. The prototype included a template for trimming stock plungers in a manner similar to that shown in FIGS. 5A 5B, and 5C so that exactly 30 mL of marrow would be processed by the system. After the marrow was inserted into the isolation container, it was spun in the centrifuge for 15 minutes at 740 RPM (125 g). Thus, the force applied to the sample was slightly slower and longer than the standard technique because of issues with the plunger moving out of position due to centrifugal force. After the separation, the isolation container was removed from the centrifuge. The operator used a syringe and needle to contemporaneously draw off the buffy coat. Both 5 and 10 mL syringes and the needles were used for the examples.
Results Four samples were processed according to the two techniques described above. As shown in FIG. 11, the number of nucleated cells extracted from each sample with the disclosed technique exceeded the number of nucleated cells extracted using conventional techniques. As shown in FIG. 12, the disclosed techniques resulted in a 1.7 fold to 4.6 fold increase in nucleated cell recovery. See also Table 1 below.

TABLE 1

| | Nucleated Cells/30 cc Sample | |
|---|---|---|
| | Conventional Technique | Disclosed Technique |
| Sample 1 | 197.5 $e^6$ NCs/30 cc | 339.0 $e^6$ NCs/30 cc |
| Sample 2 | 56.7 $e^6$ NCs/30 cc | 109.5 $e^6$ NCs/30 cc |
| Sample 3 | 102.0 $e^6$ NCs/30 cc | 476.0 $e^6$ NCs/30 cc |
| Sample 4 | 130.2 $e^6$ NCs/30 cc | 360.0 $e^6$ NCs/30 cc |

What is claimed is:

1. An apparatus for processing a blood sample comprising:
   an isolation container comprising a side wall defining an interior volume, wherein the interior volume comprises;
     a proximal reservoir having a select diameter;
     a medial reservoir in fluid communication with the proximal reservoir, the medial reservoir having a select diameter which is less than the select diameter of the proximal reservoir;
     a distal reservoir positioned opposite the medial reservoir from the proximal reservoir in fluid communication with the medial reservoir, the distal reservoir having a select diameter which is greater than the select diameter of the medial reservoir;
     a port passing through a portion of the isolation container side wall defining the medial reservoir, wherein the port opens directly into the medial reservoir from outside the isolation container, such that the port does not pass through the proximal reservoir or the distal reservoir, wherein the apparatus further comprises;
   a plunger in sealing and slideable engagement with a portion of the side wall of the isolation container defining the distal reservoir; and
   a coupling in fluid communication with the proximal reservoir.

2. The apparatus for processing a blood sample of claim 1 wherein the plunger comprises:
   a sealing element; and
   a handle engaged with the sealing element wherein a portion of the handle extends beyond a distal end of the portion of the side wall surface of the isolation container defining the distal reservoir.

3. The apparatus for processing a blood sample of claim 2 wherein at least a portion of the handle may be selectively removed from the sealing element of the plunger.

4. The apparatus for processing a blood sample of claim 3 wherein the handle comprises a plurality of perforations defining at least one break-line at which a portion of the handle may be selectively removed from a remaining portion of the handle.

5. The apparatus for processing a blood sample of claim 4 wherein the plurality of perforations defines at least two break-lines which define a break-plane.

6. The apparatus for processing a blood sample of claim 5 wherein the break-plane is co-planer with a plane defined by the distal side wall surface of the distal reservoir, when the plunger is positioned to define a selected volume within the isolation container.

7. The apparatus for processing a blood sample of claim 1 wherein the location of the port may be translated axially toward the proximal reservoir or axially toward the distal reservoir.

8. The apparatus for processing a blood sample of claim 1 further comprising an inner lumen having an opening at one end in fluid communication with the medial reservoir.

9. The apparatus for processing a blood sample of claim 8 wherein the position of the inner lumen opening may be translated within the medial reservoir axially toward the proximal reservoir or axially toward the distal reservoir.

10. The apparatus for processing a blood sample of claim 1 wherein the portion of the side wall of the isolation container defining the medial reservoir comprises a transparent material.

11. A method of processing a blood sample into constituents comprising:
drawing blood from a mammal into an isolation container comprising an isolation container side wall defining an interior volume, wherein the interior volume comprises;
a proximal reservoir having a select diameter;
a medial reservoir in fluid communication with the proximal reservoir, the medial reservoir having a select diameter which is less than the select diameter of the proximal reservoir;
a distal reservoir positioned opposite the medial reservoir from the proximal reservoir in fluid communication with the medial reservoir, the distal reservoir having a select diameter which is greater than the select diameter of the medial reservoir;
a port passing through a portion of the isolation container side wall defining the medial reservoir, wherein the port opens directly into the medial reservoir from outside the isolation container, such that said port that does not pass through the proximal reservoir or the distal reservoir;
a plunger in sealing and slideable engagement with a portion of the sidewall of the isolation container defining the distal reservoir; and
a coupling in fluid communication with the proximal reservoir;
sealing the proximal end of the proximal reservoir;
engaging the isolation container with a centrifuge;
centrifuging the blood within the isolation container; and
withdrawing a selected blood constituent from the medial reservoir through the port.

12. The method of claim 11 wherein the selected blood constituent is a buffy coat.

13. The method of claim 11 further comprising drawing blood into the isolation chamber by distally moving the plunger within the distal reservoir.

14. The method of claim 13 further comprising separating a portion of a handle from a sealing element of the plunger after blood has been drawn into the isolation chamber.

15. The method of claim 14 wherein the handle comprises a plurality of perforations defining at least one break-line and wherein the method comprises removing a portion of the handle from the remaining portion of the handle at the break-line.

16. The method of claim 15 wherein the plurality of perforations define at least two break-lines which define a break-plane and the method further comprises:
removing a portion of the handle at the break lines; and
causing the break-plane to become co-planer with a plane defined by a distal end portion of the side wall of the isolation container defining the distal reservoir, to define a selected volume within the isolation container.

17. The method of claim 12 further comprising withdrawing the buffy coat through the port.

18. The method of claim 12 further comprising:
translating the location of the port axially toward the proximal reservoir or axially toward the distal reservoir; and
withdrawing the buffy coat from the medial reservoir.

19. The method of claim 12 further comprising withdrawing the buffy coat through an inner lumen having an opening at one end in fluid communication with the medial reservoir.

20. The method of claim 19 further comprising:
translating the location of the inner lumen opening axially toward the proximal reservoir or axially toward the distal reservoir; and
withdrawing the buffy coat through the inner lumen from the medial reservoir.

21. The method of claim 11 further comprising viewing the buffy coat through a transparent side wall defining the medial reservoir.

22. The method of claim 11 further comprising selecting an isolation container from a plurality of isolation containers having selected unique interior volumes.

* * * * *